United States Patent [19]
Le Men et al.

[11] 3,987,048
[45] Oct. 19, 1976

[54] PROCESS FOR THE PREPARATION OF VINCADIFFORMINE AND DERIVATIVES

[75] Inventors: Jean Georges Le Men; Louisette Marie Therese Olivier nee Le Men; Jean Lévy; Marie Christine Appert-Collin nee Levy, all of Reims, France; Jean Alfred Alphonse Joseph Hannart, Brussels, Belgium

[73] Assignee: Omnium Chimique Societe Anonyme, Brussels, Belgium

[22] Filed: June 18, 1974

[21] Appl. No.: 480,322

[30] Foreign Application Priority Data

June 22, 1973  Belgium .............................. 801324

[52] U.S. Cl. ...................... 260/287 P; 260/283 SY; 260/293.54; 260/326 N; 326/A

[51] Int. Cl.² ............... C07D 471/16; C07D 519/04
[58] Field of Search .................... 260/287 R, 287 P Primary Examiner—Nicholas S. Rizzo
Assistant Examiner—David E. Wheeler
Attorney, Agent, or Firm—Pollock, Vande Sande & Priddy

[57] ABSTRACT

In the preparation of vincadifformine and derivatives thereof, such as 3-oxo-1,2-dehydroaspidospermidine and 1,2-dehydro-aspidospermidine, 2-hydroxy-tryptamine or a derivative thereof substituted in the benzene ring is condensed with dimethyl 4-ethyl-4-formyl-pimelate to form an oxindolic lactam-ester as the first step of the process. By means of this process, vincadifformine and its derivatives can be obtained in a smaller number of steps than in known processes.

18 Claims, 1 Drawing Figure

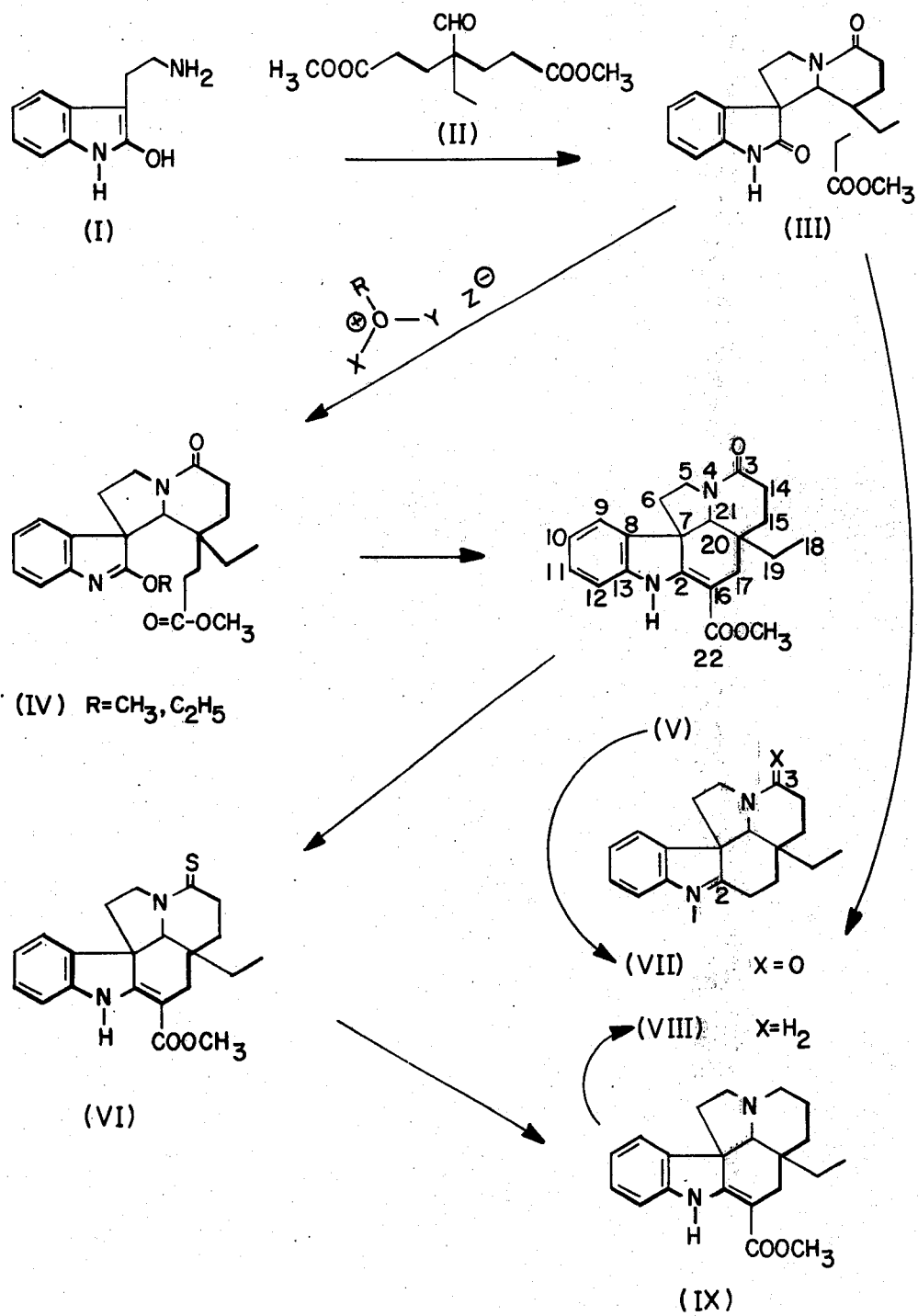

PROCESS FOR THE PREPARATION OF VINCADIFFORMINE AND DERIVATIVES

The present invention is concerned with the preparation of vincadifformine and derivatives thereof.

More particularly, the present invention is concerned with the preparation of compounds of formula 1:

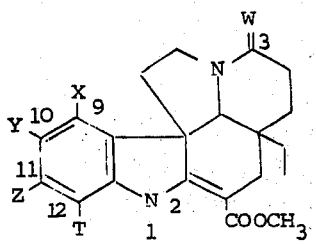

1 in which W is O, S or H,H, and X, Y, Z and T are hydrogen or any one or two of X, Y, Z and T are hydroxy or alkoxy groups, the remainder being hydrogen, and of compounds of formula 2:

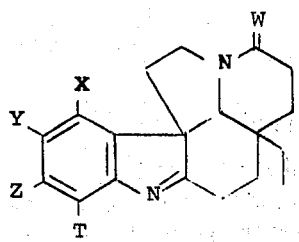

2 in which W, X, Y, Z and T have the above-stated meanings. The compounds of formula 2 are derived from those of formula 1 by loss of the —COOCH$_3$ substituent and isomerisation of the double bond.

The compounds of formulae 1 and 2 are starting materials for the preparation of alkaloids of the vincamine group according to the processes described in French Pat. Nos. 71.47731, 72.32033, 72.12838, 72.29779, and 72.12181.

Two of the compounds of formula 1 have been prepared by Kutney, Chan, Failli, Fromson, Gletsos and Nelson (J.A.C.S., 1968, 90, 3891), namely vincadifformine (1: W = H,H; X = Y = Z = T = H) and 11-methoxy-vincadifformine (1: W = H,H; X = Y = T = H; 2 = OCH$_3$).

3-Oxo-1,2-dehydro-aspidospermidine (2: W = O; X = Y = Z = T = H) has been prepared, but not characterised, by Harley-Mason and Kaplan (*Chem. Comm.*, 1967, 915) and 1,2-dehydro-aspidospermidine (2: W = H,H; X = Y = Z = T = H) by Plat and Le Men (*Tetrah. Letters*, 1962, 271). The numbering of the indolic alkaloids is in accordance with Le Men and Taylor, *Experientia*, 1965, 21, 500.

We have now developed a process which enables the compounds of formulae 1 and 2 to be obtained by a smaller number of stages than in the previously described processes mentioned above.

According to the present invention, in a process for the preparation of compounds of formulae 1 and 2, we provide the improvement which comprises condensing a 2-hydroxy-tryptamine derivative of formula 3:

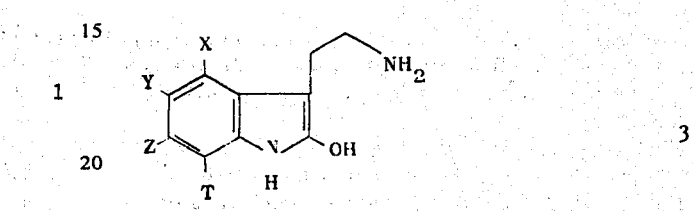

3 in which X, Y, Z and T have the specified meanings, with dimethyl 4-ethyl-4-formyl-pimelate to form an intermediate of formula 4:

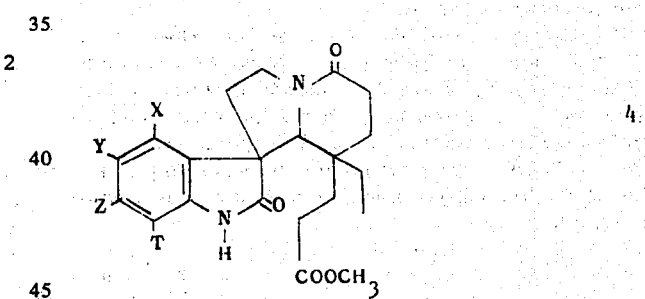

4 as the first step of the process.

This condensation reaction is preferably carried out in two stages, the first comprising heating the reactants in the presence of an organic solvent capable of forming an azeotrope with the water liberated by the condensation, such as benzene or xylene, and removing such water by azeotropic distillation, and the second comprising heating in the presence of an acid, such as acetic acid.

The compound of formula 4 obtained is reacted, in a second step, with a Meerwein reagent containing a methyl or ethyl group, such as trimethyloxonium fluoroborate or triethyloxonium fluoroborate, in order to obtain an iminoether of formula 5:

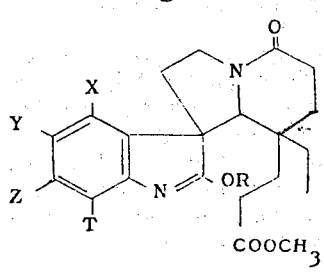

in which R is methyl or ethyl. The compound of formula 5 in which R is ethyl can also be obtained by reacting the compound of formula 4 with ethyl polyphosphate.

In a third step, the compound of formula 5 is cyclized by treatment with a strong base, such as sodium hydride, in an aprotic solvent, such as dimethyl sulphoxide or hexamethylphosphorotriamide, in order to obtain a compound of formula 1 in which W is O.

In a fourth step, the compound of formula 1 in which W is O is reacted with phosphorus pentasulphide in order to obtain a compound of formula 1 in which W is S and, in a fifth step, the latter compound may be reduced in the presence of Raney nickel in order to obtain a compound of formula 1 in which W is H,H.

Treatment of a compound of formula 1 (whatever the value of W) with an inorganic acid at elevated temperature, for example as described by Plat and Le Men, Tetrah. Letters, 1962, 272, gives the corresponding compound of formula 2.

According to a variant of the above-described procedure, a compound of formula 2 in which W is O can be obtained directly from a compound of formula 4 by treating the latter with a dehydrating agent, such as polyphosphoric acid, at elevated temperature.

In order that the invention may be more fully understood, the following examples are given by way of illustration only:

EXAMPLE 1

Oxindolic Lactam-ester (4; X = Y = Z = T = H)

A solution of 176 g of 2-hydroxy-tryptamine and 268 g of dimethyl 4-ethyl-4-formyl-pimelate in 3 liters of anhydrous benzene was heated for 4 hours under reflux, azeotropic removal of the water formed being effected by means of a Dean-Stark apparatus, and the reaction mixture was then evaporated to dryness.

The residue was dissolved in 2 liters of glacial acetic acid and heated at reflux temperature for 1½ hours under nitrogen. The solution was then concentrated under reduced pressure, diluted with 3 liters of water, and extracted with chloroform. The organic phase was washed with water, dried over magnesium sulphate, and evaporated to give 266 g of a translucent lacquer which was chromatographed in benzene solution on a silica column.

The following were successively eluted:
i. 37 g of a first compound of formula 4 which was crystallised in methanol (this product was not used in the subsequent reactions).

m.p. 219°–223° C. U.V. max. nm (log $\epsilon$): 215 (4.39), 255 (4.11), 280 (3.92). I.R. (KBr, $cm^{-1}$): 1610, 1720, 1730. Mass spectrum: $M^+$ 370. Analysis calculated for $C_{21}H_{26}O_4N_2$:

|  | C | H | N |
|---|---|---|---|
| Calculated % | 68.08 | 7.07 | 7.56 |
| Found % | 67.99 | 7.04 | 7.58 | ii. 230 g of a second compound of formula 4 which was crystallised in methanol (this product was used in the subsequent reactions).

m.p. 253°–256° C. U.V. max. nm (log $\epsilon$): 215 (4.44), 254 (3.78), 286 (3.06). I.R. (KBr, $cm^{-1}$): 1605, 1725. Mass spectrum: $M^+$ 370. Analysis calculated for $C_{21}H_{26}O_4N_2$:

|  | C | H | N |
|---|---|---|---|
| Calculated % | 68.08 | 7.07 | 7.56 |
| Found % | 68.12 | 7.10 | 7.49 |

EXAMPLE 2

Iminoether (5; R = $C_2H_5$, X = Y = Z = T = H)

a. 12 g of the major product of Example 1 were mixed with 20 g of ethyl polyphosphate and the mixture was allowed to stand for 3 days at 15°–30° C. After dilution of the mixture with water and extraction with methylene chloride, the iminoether was separated. The product was crystallised in ethanol to give 7.2 g of crystalline product.

m.p. 173°–7° C. U.V. max. nm: 220, 262, 270 (infl.), 285 (infl.). I.R. ($CHCl_3$, $cm^{-1}$): 1640, 1710. Mass spectrum: $M^+$ 398 Analysis calculated for $C_{23}H_{30}O_4N_2$:

|  | C | H | N |
|---|---|---|---|
| Calculated % | 69.32 | 7.58 | 7.02 |
| Found % | 69.36 | 7.60 | 7.10 | b. 20 g of the major product of Example 1 were mixed with 30 ml of triethyloxonium fluoroborate in 200 ml of anhydrous methylene chloride and the mixture was allowed to stand for 3 days at 15°–30° C. The mixture was then washed with water, dried, and the methylene chloride evaporated off to give a dry residue. 20 g of the iminoether 5 (R = $C_2H_5$; X = Y = Z = T = H) were obtained.

EXAMPLE 3

Iminoether (5; R = CH$_3$; X = Y = Z = T = H)

14 g of the major product of Example 1 were treated as described in Example 2 b), but using trimethyloxonium fluoroborate instead of triethyloxonium fluoroborate.

13.5 g of the iminoether 5 (R = CH$_3$; X = Y = Z = T = H) were obtained in the form of a translucent lacquer which was homogeneous when subjected to thin layer chromatography.

U.V. max. nm: 220, 260, 269 (infl.), 285 (infl.). I.R. (CHCl$_3$, cm$^{-1}$): 1640, 1710. Mass spectrum: M$^+$ 384. Analysis calculated for C$_{22}$H$_{28}$O$_4$N$_2$:

|  | C | H | N |
|---|---|---|---|
| Calculated % | 68.72 | 7.34 | 7.28 |
| Found % | 68.74 | 7.39 | 7.25 |

EXAMPLE 4

3-Oxo-vincadifformine (1; W = O; X = Y = Z = T = H)

A mixture of a solution of 24 g of the iminoether 5 (R = CH$_3$; X = Y = Z = T = H) in 100 ml of dimethyl sulphoxide and 30 g of a 70% suspension of sodium hydride in paraffin oil, was heated to 100° C under nitrogen for 2 hours.

After dilution of the mixture with water and extraction with methylene chloride, 18 g of an amorphous residue were obtained and this product was then chromatographed, in solution in benzene, on a silica column to give 12 g of amorphous 3-oxo-vincadifformine.

U.V. max. nm: 220, 298, 330. I.R. (CHCl$_3$, cm$^{-1}$): 1610, 1650. Mass spectrum: M$^+$ 352. Analysis calculated for C$_{21}$H$_{24}$O$_3$N$_2$:

|  | C | H | N |
|---|---|---|---|
| Calculated % | 71.56 | 6.86 | 7.94 |
| Found % | 71.51 | 6.84 | 7.90 |

EXAMPLE 5

3-Thio-vincadifformine (1; W = S; X = Y = Z = T = H)

A solution of 34 g of 3-oxo-vincadifformine in 500 ml of tetrahydrofuran was agitated for 4 hours at 15°–30° C with 34 g of phosphorus pentasulphide. After dilution of the reaction mixture with water and extraction with methylene chloride, 28 g of 3-thio-vincadifformine were obtained.

U.V. max. nm: 223, 273, 295 (infl.), 328. I.R. (CHCl$_3$, cm$^{-1}$): 1605, 1680. Mass spectrum: M$^+$ 368. Analysis calculated for C$_{21}$H$_{24}$O$_2$N$_2$S:

|  | C | H | N |
|---|---|---|---|
| Calculated % | 68.44 | 6.56 | 7.60 |
| Found % | 68.49 | 6.61 | 7.58 |

EXAMPLE 6

Vincadifformine (1; W = H,H; X = Y = Z = T = H)

A solution of 28 g of 3-thio-vincadifformine in 500 ml of tetrahydrofuran was heated at reflux temperature under nitrogen with 200 g of Raney nickel for 78 hours. The reaction mixture was filtered, the filtrate was diluted with water, rendered alkaline by the addition of sodium carbonate, and extracted with methylene chloride to give 22 g of vincadifformine which was purified by chromatography, in solution in benzene, on a silica column and identified by comparison with an authentic specimen of (±) vincadifformine.

EXAMPLE 7

3-Oxo-1,2-dehydro-aspidospermidine (2; W = O; X = Y = Z = T = H)

a. A solution of 1 g of 3-oxo-vincadifformine in 10 ml of concentrated hydrochloric acid was heated at 100° C for 3 hours under nitrogen. The reaction mixture was diluted with water, rendered alkaline, and extracted with methylene chloride, to give 0.8 g of 3-oxo-1,2-dehydroaspidospermidine.

U.V. max. nm: 221, 268. I.R. (CHCl$_3$, cm$^{-1}$): 1650, 1670. Mass spectrum: M$^+$ 294. Analysis calculated for C$_{19}$H$_{22}$ON$_2$:

|  | C | H | N |
|---|---|---|---|
| Calculated % | 77.51 | 7.53 | 9.51 |
| Found % | 77.48 | 7.49 | 9.55 | b. 5 g of the oxindolic lactam-ester (4; X = Y = Z = T = H) were intimately mixed with 40 g of polyphosphoric acid and the mixture was heated to 120°–130° C under nitrogen for 2 hours with mechanical agitation.

The reaction mixture was diluted with water and extracted with methylene chloride to give 3.4 g of a colourless lacquer which was purified by chromatography in solution in benzene on a silica column to give 2.7 g of 3-oxo-1,2-dehydro-aspidospermidine.

What is claimed is:

1. A process for the preparation of compound of the formula:

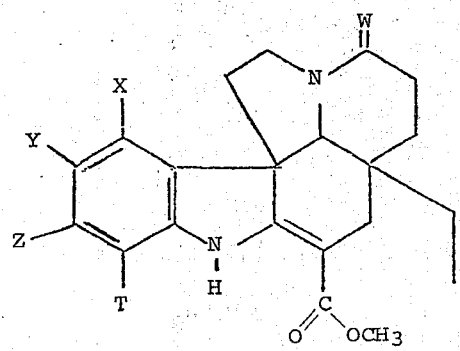

wherein W is O; each X, Y, Z, and T individually is selected from the group consisting of hydrogen, hydroxy, and lower alkoxy provided that at least two of X, Y, Z, and T are hydrogen, which comprises the steps of:

A. condensing a 2-hydroxy-tryptamine compound of the formula:

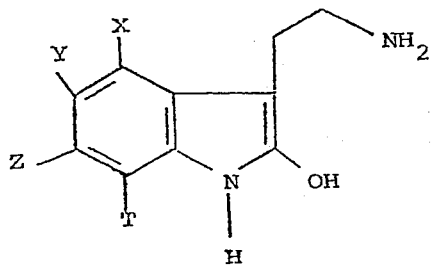

in which X, Y, Z, and T have the above-specified meanings with dimethyl 4-ethyl 4-formyl-pimelate to thereby form an intermediate of the formula:

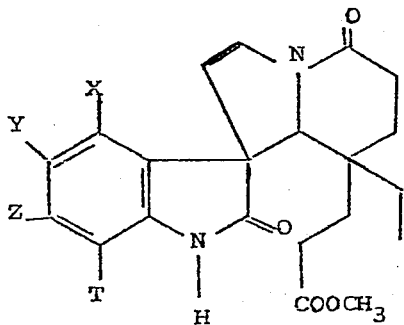

in which X, Y, Z, and T have the above-specified meanings;

B. reacting the compound of formula 3 with a member selected from the group consisting of ethyl polyphosphate, trimethyl oxonium fluoroborate, triethyl oxonium fluoroborate and mixtures thereof to thereby form an iminoether of the formula:

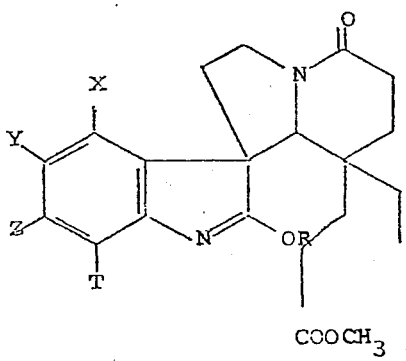

in which R is methyl or ethyl and X, Y, Z, and T have the above-specified meanings;

C. treating the compound of formula 4 with sodium hydride in an aprotic solvent to thereby cyclize said compound of formula 4 into a compound of formula 1 hereinabove where W is oxygen and X, Y, Z, and T have the above-specified meanings to thereby obtain compound of formula 1; and wherein all of the steps include at each step isolation of the product which is obtained.

2. The process of claim 1 wherein said condensation is effected in two stages, the first of which the starting materials are heated in the presence of an aprotic solvent capable of forming an azeotrope with water and effecting azeotropic distillation, and in the second of which the product of the first stage is heated in the presence of acetic acid.

3. The process of claim 2 wherein said solvent is benzene or toluene.

4. The process of claim 1 wherein said compound of formula 4 is obtained by reacting the compound of formula 3 with trimethyl-oxonium fluoroborate or triethyloxonium fluoroborate.

5. The process of claim 1 wherein in step (B) the compound of formula 4 is obtained by reacting the compound of formula 3 with ethyl polyphosphate and wherein R is ethyl.

6. A process according to claim 1 wherein the aprotic solvent is dimethylsulfoxide or hexamethylphosphorotriamide.

7. The process for the preparation of compound of the formula:

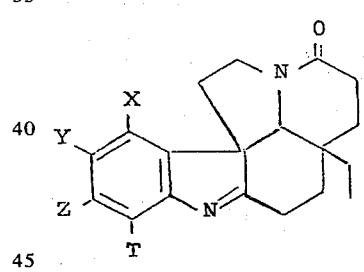

which includes the step of treating the compound of formula 1 obtained by the process of claim 1 with hydrochloric acid to obtain the compound of formula 7.

8. The process for the preparation of the compound of the formula:

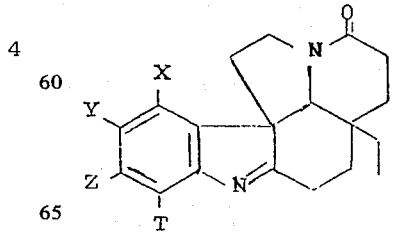

wherein each X, Y, Z, and T individually is selected from the group consisting of hydrogen, hydroxy, and lower alkoxy provided that at least two of X, Y, Z, and T are hydrogen which comprises the steps of:

A. condensing a 2-hydroxy-tryptamine compound of the formula:

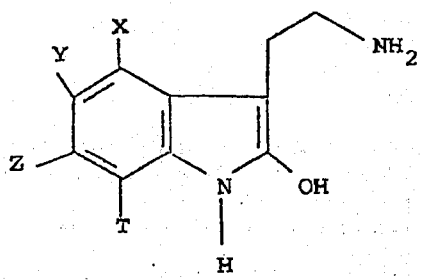

2 in which X, Y, Z, and T have the specified meaning with dimethyl 4-ethyl 4-formyl-pimelate to thereby form an intermediate of the formula:

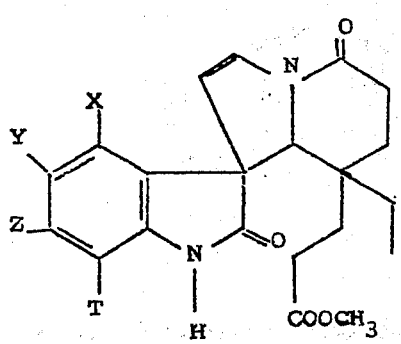

3 in which X, Y, Z, and T have the above-specified meanings;

B. treating the compound of formula 3 obtained from step (A) above with polyphosphoric acid at elevated temperature to thereby provide said compound of formula 7; and wherein all of the steps include at each step isolation of the product which is obtained.

9. The process of claim 8 wherein step (A) is effected in two-step sequence, wherein the first step consists of heating in an aprotic solvent capable of forming an azeotrope with water, and the second consists of heating with acetic acid, to form an intermediate of the formula:

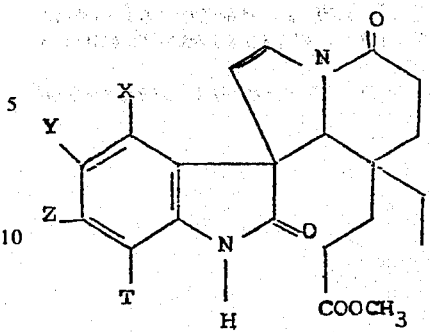

3 where X, Y, Z, and T have the specified meanings.

10. The process of claim 9 wherein said aprotic solvent is benzene or toluene.

11. A process for the preparation of compound of the formula:

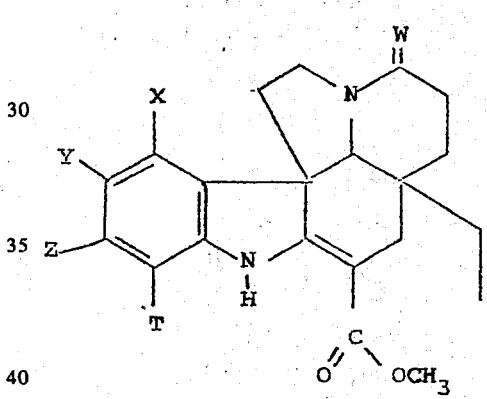

5 wherein W is S; each X, Y, Z, and T individually is selected from the group consisting of hydrogen, hydroxy, and lower alkoxy provided that at least two of X, Y, Z, and T are hydrogen, which comprises the steps of treating the compound of formula 1 obtained by the process of claim 1 with phosphorus pentasulfide into a compound of formula 5 wherein W is S and X, Y, Z, and T have the above-specified meanings to thereby obtain the compound of formula 5; and wherein all of the steps include at each step isolation of the product which is obtained.

12. The process of claim 11 wherein said condensation of step (A) is effected in two stages, the first of which the starting materials are heated in the presence of an aprotic solvent capable of forming an azeotrope with water and effecting azeotropic distillation, and in the second of which the product of the first stage is heated in the presence of acetic acid.

13. The process of claim 12 wherein said aprotic solvent capable of forming an azeotrope with water is benzene or toluene.

14. The process for the preparation of compound of the formula:

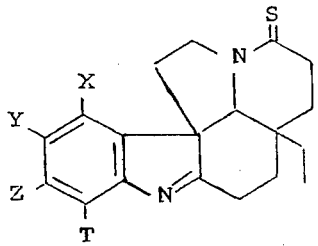

8 which includes treating the compound of formula 5 obtained by the process of claim 11 with hydrochloric acid to obtain the compound of formula 8.

15. A process for the preparation of compound of the formula:

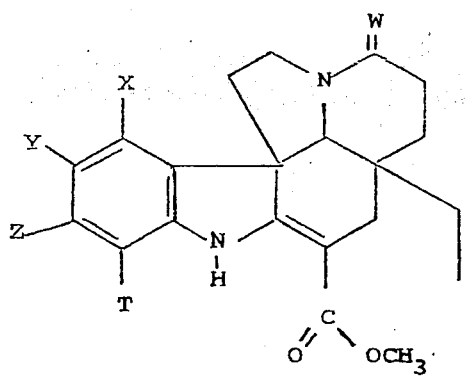

5 wherein W is two hydrogen atoms; each X, Y, Z, and T individually is selected from the group consisting of hydrogen, hydroxy, and lower alkoxy provided that at least two of X, Y, Z, and T are hydrogen; which comprises treating the compound of formula 5 obtained by the process of claim 11 with hydrogen in the presence of Raney nickel into a compound of formula 6 wherein W is two hydrogen atoms, and X, Y, Z, and T have the above-specified meanings to thereby obtain the compound of formula 6; and wherein all of the steps include at each step isolation of the product which is obtained.

16. The process for the preparation of compound of the formula:

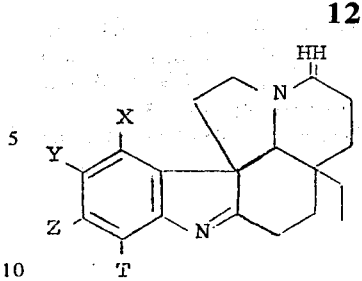

9 which includes treating the compound of formula 7 obtained by the process of claim 15 with hydrochloric acid to obtain the compound of formula 9.

17. The process for the preparation of compound of the formula:

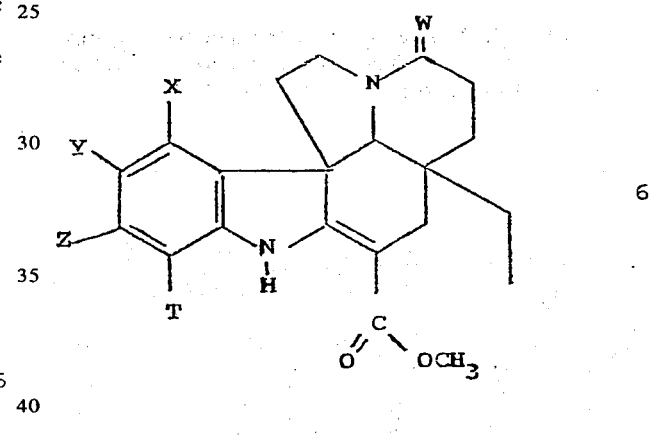

6 wherein W is two hydrogen atoms; each X, Y, Z, and T individually is selected from the group consisting of hydrogen, hydroxy, and lower alkoxy provided that at least two of X, Y, Z, and T are hydrogen; which comprises the steps of:

A. condensing 2-hydroxy-tryptamine of the formula:

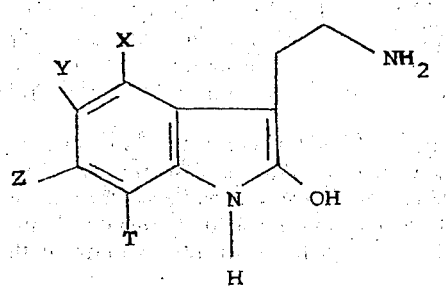

2 in which X, Y, Z, and T have the specified meanings, in a two-step sequence with dimethyl-4-ethyl-4-formyl pimelate, wherein the first step consists of heating in an aprotic solvent capable of forming an azeotrope with water, and the second consists of heating with acetic acid, to form an intermediate of the formula:

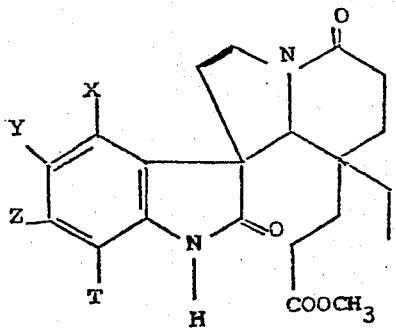

3 where X, Y, Z, and T have the specified meanings;

B 1. reacting the compound of formula 3 with a reagent selected from the group consisting of ethyl polyphosphate, trimethyloxonium fluoroborate and triethyloxonium fluoroborate whereby the iminoether of the formula:

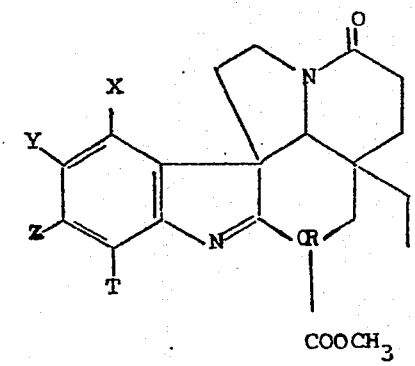

4 is obtained in which R is methyl or ethyl and X, Y, Z, and T have the specified meanings;

B 2. treating the compound of formula 4 with a sodium hydride in the presence of an aprotic solvent whereby there is obtained a compound of the formula:

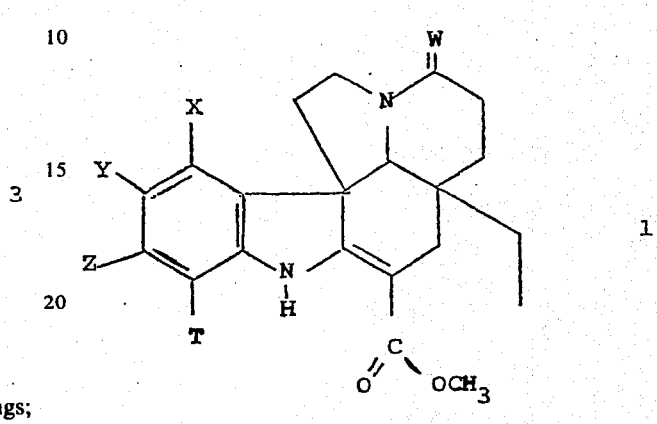

1 wherein W is oxygen and X, Y, Z, and T have the above-specified meanings;

B 3. reacting the compound in (B) (2) with phosphorous pentasulfide whereby there is formed a compound of formula 1 where W is sulfur;

B 4. reducing the compound obtained in (B) (3) with hydrogen in the presence of Raney nickel whereby there is obtained the compound of formula 1, where W is $H_2$;

B 5. treating the compound obtained in (B) (4) with hydrochloric acid at elevated temperatures whereby there is obtained a compound of formula 9; wherein all of the above steps further include isolation of the product at each step.

18. The process of claim 16 wherein said aprotic solvent capable of forming an azeotrope with water is benzene or toluene.

* * * * *